United States Patent
Hayashi

(10) Patent No.: US 6,244,713 B1
(45) Date of Patent: Jun. 12, 2001

(54) OPTOMETRIC CHART PRESENTING APPARATUS

(75) Inventor: Akihiro Hayashi, Toyokawa (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/544,633

(22) Filed: Apr. 6, 2000

(30) Foreign Application Priority Data

| Apr. 6, 1999 | (JP) | 11-099338 |
| Nov. 4, 1999 | (JP) | 11-313153 |

(51) Int. Cl.⁷ .................................................. A61B 3/02
(52) U.S. Cl. ............................................................. 351/243
(58) Field of Search .................................. 351/237, 238, 351/239, 240, 243, 244, 245, 246

(56) References Cited

U.S. PATENT DOCUMENTS

| 4,597,651 | 7/1986 | Capo-Gual et al. | |
| 5,129,720 | * 7/1992 | Jovicevic | 351/243 |
| 5,471,262 | * 11/1995 | Trokel | 351/239 |
| 5,929,972 | * 7/1999 | Hutchinson | 351/237 |

FOREIGN PATENT DOCUMENTS

| 0 578 236 A1 | 1/1994 | (EP) . |
| 2754034 | 3/1998 | (JP) . |
| 10-276981 | 10/1998 | (JP) . |

OTHER PUBLICATIONS

Abstract, JP2268732A2: Inspection Instrument with Binocular Vision (Apr. 11, 1989).

* cited by examiner

Primary Examiner—George Manuel
(74) Attorney, Agent, or Firm—Finnegan, Henderson, Farabow, Garrett & Dunner, L.L.P.

(57) ABSTRACT

An optometric chart presenting apparatus which has a casing provided with a pair of test windows for right eye and for left eye for presenting an optotype optically placed at a predetermined distance to an eye to be examined through at least one of the test windows within the casing, the apparatus comprising a rotating optometric chart disk having a set of optotypes for right eye and a set of optotypes for left eye on one surface thereof, a restricting device disposed on a side of the eye relative to the optotypes for restricting a visual field of the eye, and a driving device for activating rotation of the rotating optometric chart disk in order to move an intended optotype into the visual field.

19 Claims, 6 Drawing Sheets

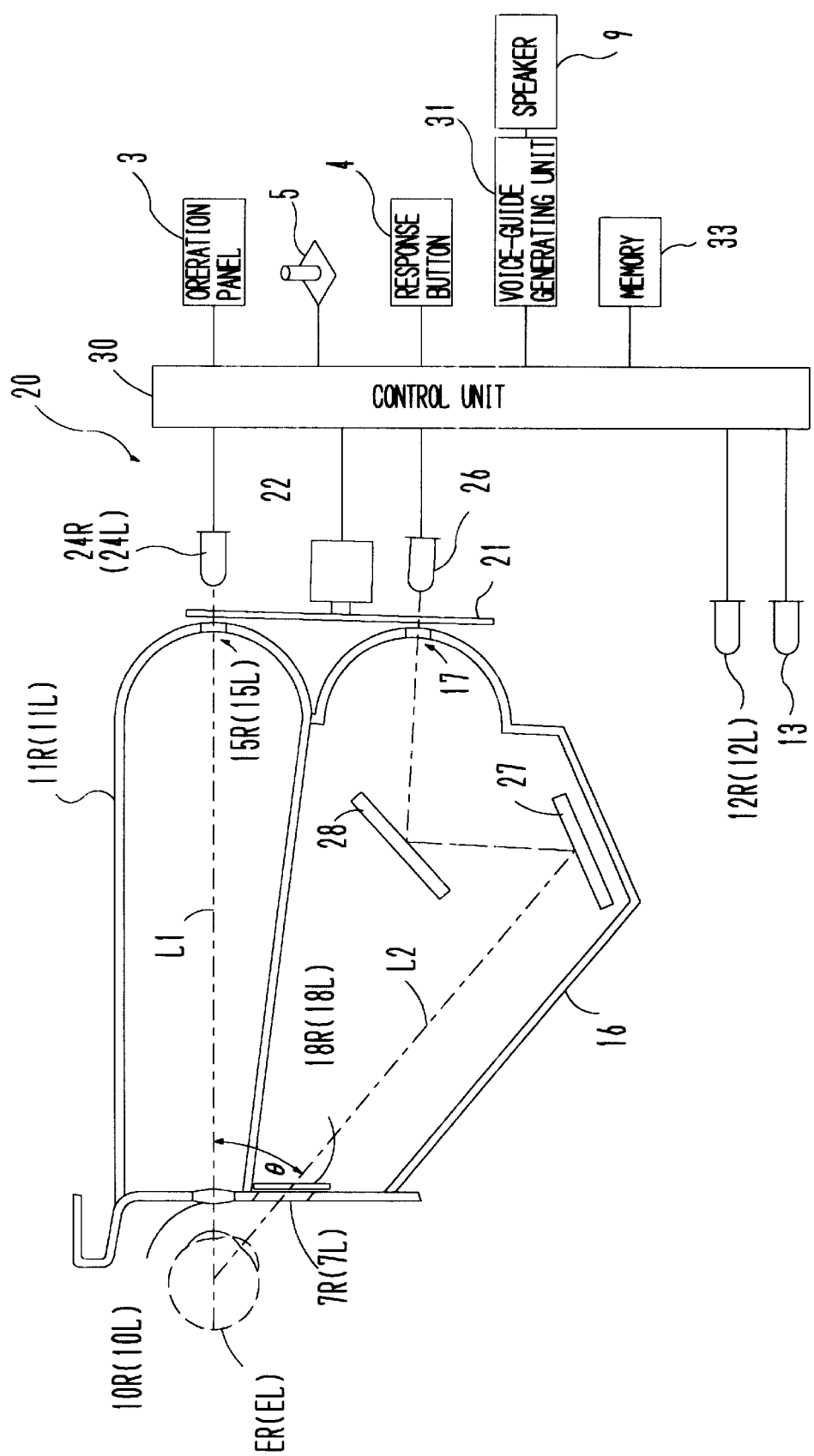
F I G. 2

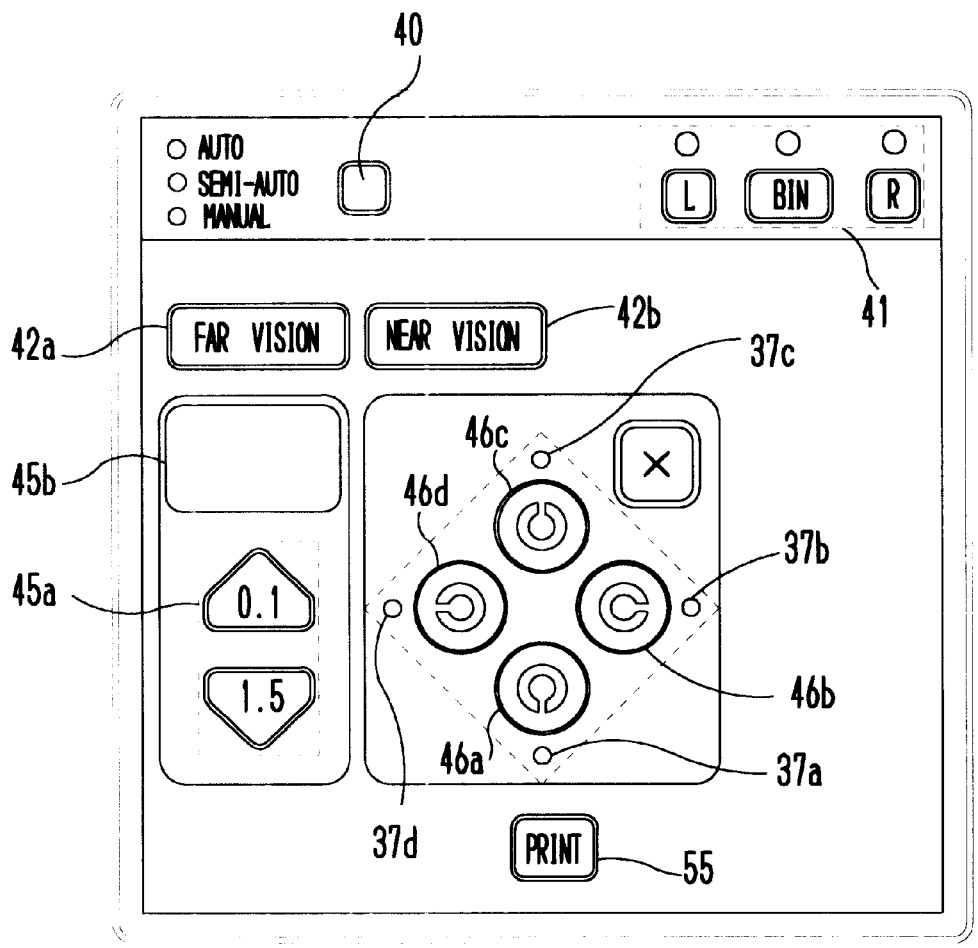
F I G . 5

OPTOMETRIC CHART PRESENTING APPARATUS

BACKGROUND OF THE INVENTION

1. Field of the Invention

The present invention relates to an optometric chart presenting apparatus used in visual acuity testing and the like.

2. Description of Related Art

One conventionally known optometric chart presenting apparatus is provided with binocular sight windows which eyes to be examined look into. Optotypes are presented to the eyes through these sight windows within a casing and the eyes are made to observe the optotypes so that visual function of the eyes such as visual acuity is examined. Conventionally, this type of apparatus presents optotypes in the following three ways.

(a) One of various optotypes illustrated on a rotating optometric chart disk or the like is placed in the center of right and left optical paths, and a luminous flux of an optotype is guided to right and left sight windows with the use of a prism or a mirror. As the result, the optotype can be presented to the both eyes. The testing distance is adjusted to a predetermined distance for far vision by a convex lens disposed at some midpoint along the optical paths.

(b) Similarly to the above mentioned way (a), one of the optotypes is placed in the center of the right and left optical paths. In addition, large convex lenses are disposed to cover each of the sight windows for right and left. Due to this configuration, it is possible to present the optotype to the both eyes optically at a predetermined distance for far vision.

(c) Right and left optical paths are configured to be independent of each other and an optotype presentation window is disposed to each path. By placing same optotypes alternatively in each of the windows, the optotypes are presented to the both eyes. In this way, images of the optotypes look fused into one image on binocular observation. The testing distance is adjusted to a predetermined distance for far vision by respective convex lenses disposed at some midpoint along each of the optical paths for right eye and for left eye (at each sight window, for example).

However, the ways of presenting optotypes as described above have following disadvantages. That is, the above-mentioned way (a) requires optical elements such as a prism and a mirror for guiding one luminous flux of an optotype to the both eyes, which inevitably results in higher cost of the apparatus. Also, the above-mentioned way (b) requires a large-sized convex lens, which also raise the cost.

According to the above-mentioned way (c), although the apparatus can be comprised of minimum optical elements, it needs to be configured to present the same optotypes in both right and left presenting windows. To meet this end, the apparatus may be configured to individually place same optotypes alternately in each presenting window with the use of two rotating optometric disks. Yet, in the case of rotating the two rotating optometric disks individually, it is extremely difficult to stop the rotating optometric disks in such a manner that optotypes for right and for left come in the same relative positions to the respective windows. If the optotypes for right and for left are stopped at different relative positions, images of the optotypes may not be fused into one at the time of observing the optotypes with both eyes. As the result, examinations of visual function can not be carried out accurately. In addition, provision of two rotating disks and motors to make the rotation results in higher cost and a larger apparatus.

Further, presenting far vision optotypes (far vision examination) and presenting near vision optotypes (near vision examination) by this type of apparatus are carried out owing to the following configurations.

For far vision measurement in the case of above way (c), the convex lenses disposed at the right and left sight windows functions to present optotypes optically at a predetermined distance for far vision in the casing. For near vision measurement, by removing the convex lenses that are disposed at the sight windows for right and left from the optical paths, or by replacing the lenses, optotypes are presented- at a predetermined distance for near vision in the casing.

However, the above type of apparatus has disadvantages as follows. That is, it is configured that an examinee observes optotypes presented ahead of him through the same sight windows in both types of measurement for far vision and for near vision. Due to this configuration, it is nearly impossible to measure near vision of a patient wearing a progressive addition lens, a bifocal lens or the like on downgaze. It is true that the patient manages to look at optotypes in the front through a near portion of the progressive addition lens or the bifocal lens by turning his face upward to tilt his head. Yet, the patient is forced to take an uncomfortable position and therefore accurate measurement can not be achieved.

In addition, when going into near vision measurement after far vision measurement, the lenses disposed at the sight windows need to be switched over. The need for a switching-over mechanism required therefore increases complexity of the configuration and also increases trouble to carry out the operation if it is done manually.

SUMMARY OF THE INVENTION

The present invention has been made in view of the above circumstances and has an object to overcome the above problems and to provide an optometric chart presenting apparatus which can stimulate fusion in binocular vision with high reliability at low cost even in the case where the apparatus is provided with optical paths for right eye and for left eye independently and configured to present optotypes to right and left eyes respectively therethrough.

Further, another object of the present invention is to provide an optometric chart presenting apparatus which can perform near vision measurement of an examinee on downgaze with the patient taking a natural position. In addition, the apparatus is capable of performing both near vision measurement and far vision measurement and yet it is simple in configuration, compact in size and inexpensive.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an optometric chart presenting apparatus which has a casing provided with a pair of test windows for right eye and for left eye for presenting an optotype optically placed at a predetermined distance to an eye to be examined through at least one of the test windows within the casing, the apparatus comprises a rotating optometric chart disk having a set of optotypes for right eye and a set of optotypes for left eye on one surface thereof, restricting means disposed on a side of the eye relative to the optotypes for restricting a visual field of the eye, and driving means for activating rotation of the rotating optometric chart disk in order to move an intended optotype into the visual field.

In another aspect of the present invention, an optometric chart presenting apparatus which has a casing provided with a pair of far vision test windows for right eye and for left eye as well as a pair of near vision test windows below the far vision windows for presenting an optotype placed optically at a predetermined distance to an eye to be examined through at least one of the test windows within the casing, the apparatus comprises a rotating optometric chart disk having sets of far vision optotypes for right eye and for left eye as wall as a set of near vision optotypes on one surface thereof, restricting means disposed on a side of the eye relative to the optotypes for restricting a visual field of the eye, and driving means for activating rotation of the rotating optometric chart disk in order to move an intended optotype into the visual field.

Further, in another aspect of the present invention, an optometric chart presenting apparatus which has a casing provided with a pear of test windows for right eye and for left eye for presenting an optotype placed optically at a predetermined distance to an eye to be examined through at least one of the test windows within the casing, the apparatus comprises a rotating optometric chart disk for right eye having a set of optotypes for right eye, a rotating optometric chart disk for left eye having a set of optotypes for left eye, restricting means disposed on a side of the eye relative to the optotypes for restricting a visual field of the eye, and driving means for activating rotation of each rotating optometric chart disk individually or in synchronism in order to move an intended optotype into the visual field. Each disk has light transmitting portions as backgrounds of the optotypes and a light shading portion which is an outer area surrounding the light transmitting portions, and a color of the light shading portion is generally the same as that of a visual field boundary area in the restricting means.

Still further, in another aspect of the present invention, an optometric chart presenting apparatus for presenting an optotype for right eye and an optotype for left eye which are placed optically at a far distance to eyes to be examined by placing the optotype alternately into a pair of optotype presenting windows for right eye and for left eye provided in the casing, the apparatus comprises a rotating optometric chart disk for right eye having a set of optotypes for right eye, a rotating optometric chart disk for left eye having a set of optotypes for left eye, and rotating means for rotating the rotating optometric chart disk in order to present an intended optotype to the eye. Each set of optotypes for right eye and for left eye are formed at each disk in such positions where positional relationship therebetween corresponds to that of the presenting windows for right eye and for left eye, whereby an optotype for right eye and an optotype for left eye to be presented in a pair simultaneously to the eyes are fused into one image on binocular observation. Each disk has light transmitting portions as backgrounds of the optotypes and a light shading portion which is an outer area surrounding the light transmitting portions and a color of the light shading portion is generally the same as that of a visual field boundary area in the restricting means Still further, in another aspect of the present invention, an optometric chart presenting apparatus for presenting an optotype for right eye and an optotype for left eye which are placed optically at a far distance to eyes to be examined by placing each optotype alternately into a pair of optotype presenting windows for right eye and for left eye provided in the casing, the apparatus comprises a rotating optometric chart disk for right eye having a set of optotypes for right eye, a rotating optometric chart disk for left eye having a set of optotypes for left eye, and rotating means for rotating the rotating optometric chart disks individually or in synchronism in order to present an intended optotype to the eye. Each set of optotypes for right eye and for left eye are formed at each disk in such positions where positional relationship therebetween corresponds to that of the presenting windows for right eye and for left eye, whereby an optotype for right eye and an optotype for left eye to be presented in a pair simultaneously to the eyes are fused into one image on binocular observation. Each disk has light transmitting portions as backgrounds of the optotypes and a light shading portion which is an outer area surrounding the light transmitting portions. A color of the light shading portion is generally the same as that of a visual field boundary area in the presenting windows.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 2 is a view showing a schematic configuration of an optical system and a control system of the apparatus;

FIG. 5 is a view showing an operation panel in detail; and

DETAILED DESCRIPTION OF THE PREFERRED EMBODIMENTS

Figure 1:
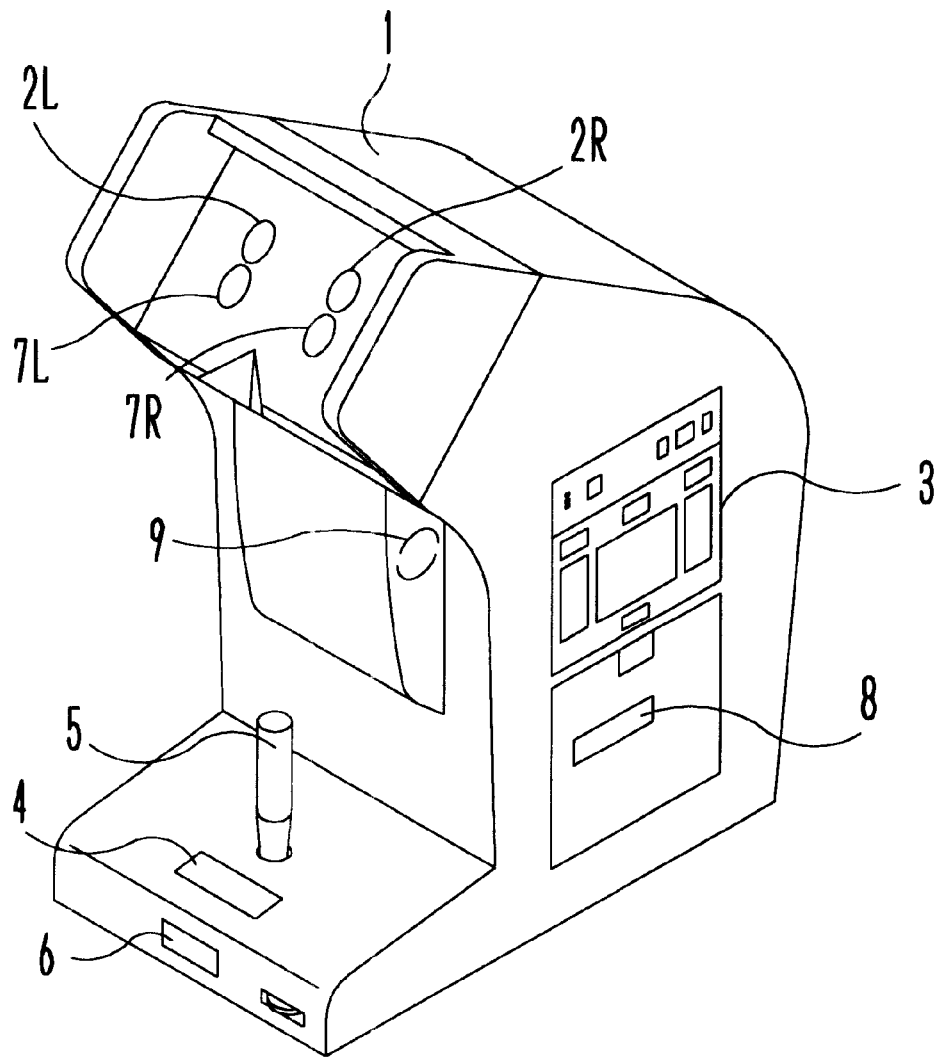
FIG. 1 is a schematic view showing an external representation of a optometric chart presenting apparatus consistent with the present invention.

A detailed description of one preferred embodiment of an optometric chart presenting apparatus for visual acuity testing embodying the present invention will now be given referring to the accompanying drawings. FIG. 1 is a schematic view showing the apparatus of the present invention.

Reference numeral 1 is a main body of the apparatus. Disposed at the top of the main body 1 are a pair of far vision windows (sight windows) 2R and 2L for right and left and a pair of near vision test windows (sight windows) 7R and 7L for right and left (the far vision windows and the near vision windows may be configured such that, instead of an upper pair and a lower pair, only one pair of the windows appear outwardly). The two pairs of test windows are for an examinee to looks into respectively when viewing an far vision optometric chart and a near vision optometric chart presented within the main body 1. The main body 1 is also provided with an operation panel 3 and a printer 8 mounted at the side thereof. Further, disposed at the lower part of the front of the main body 1 are a joystick 5 used by the examinee to indicate an orientation of a gap in an optotype presented within the main body 1, a response button 4 used by the examinee to indicate that he can not determine the orientation. 6 is a start switch used in an auto-examination mode and 9 is a speaker to output voice-guide instructions.

Figure 3:
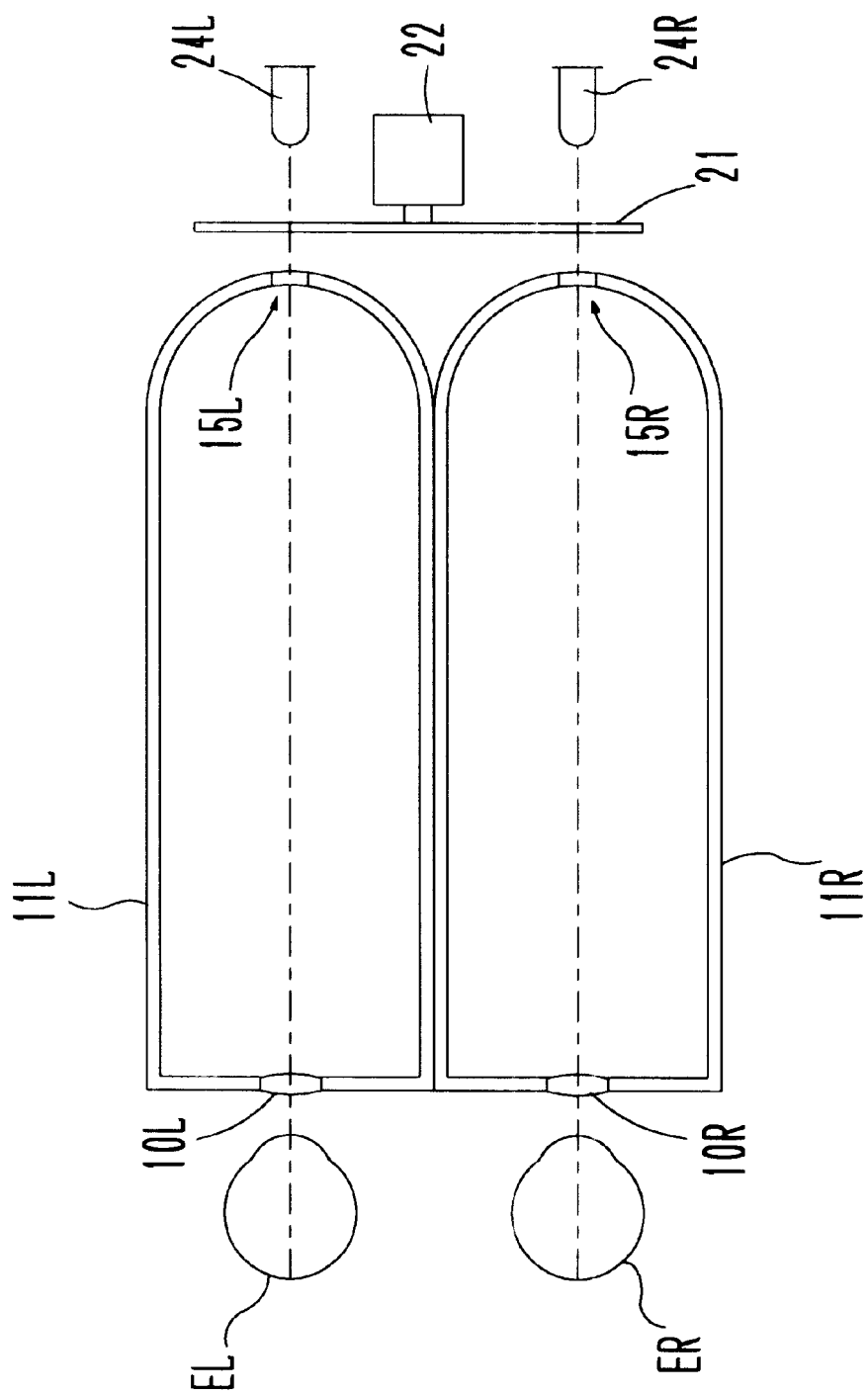
FIG. 3 is a top view showing a schematic configuration of the optical system.

FIG. 2 is a view showing a schematic configuration of an optical system located inside of the main body 1 along with a control system seen from the side. FIG. 3 is a view showing a schematic configuration of the optical system in the main body 1 seen from the top.

The far vision windows 2R and 2L for right and left are provided with lenses 10R and 10L so that optotypes presented in far vision optometric chart windows (presenting windows) 15R and 15L appear optically at a testing distance of five meters from eyes ER and EL to be examined. A pair of far vision optical paths for right and left is divided from each other by far vision inside covers 11R and 11L. Inside of the covers 11R and 11L are painted mat white and illuminated when far vision illumination LEDs 12R and 12L are turned on.

The near vision windows 7R and 7L for right and left are provided with shutters 18R and 18L so that the windows are opened or closed depending on an eye to be measured, and closed when near vision measurement is not carried out. An optical path for near vision measurement is divided from the far vision optical paths by a near vision inside cover 16. Further, an near vision optotype is presented in a near vision optometric chart window (presenting window) 17 which is arranged below the center of the far vision optometric chart windows 15R and 15L. By bending the optical path with the use of mirrors 27 and 28, the near vision optotype is presented suitably for downgazing condition at a testing distance of 40 cm from the eyes ER and EL. Inside of the cover 16 is also painted mat white and illuminated when a near vision illumination LED 13 is turned on.

An optometric chart presenting unit 20 for alternately placing optotypes in the far vision windows 15R and 15L and in the near vision window 17 comprises a rotating optometric chart disk 21, a pulse motor 22 for rotating the disk 21, a pair of far vision illumination LEDs 24R and 24L which illuminate the far vision optotypes on the disk 21, and a near vision illumination LED 26 which illuminates the near vision optotypes on the disk 21. There formed two sets of far vision optotypes for right eye and for left eye on the same side of the disk 21 such that they can be presented to the right and left eyes in pairs simultaneously. Also formed on the same side of the disk 21 are a plurality of near vision optotypes (the contents and layout the optometric chart are described later). The motor 22 for rotating the disk 21 is arranged in the middle of the right and left far vision optical paths and the near vision optical path so that the apparatus may be compact in size.

In FIG. 2, reference numeral 30 denotes a control unit for controlling the overall apparatus. The control unit 30 is connected to each LED, the motor 22, a voice-guide generating unit 31 coupled to the speaker 9, the response button 4, the joystick 5, the panel 3, the shutters 18R and 18L as well as memory 33 having examination programs stored therein.

Figure 4:
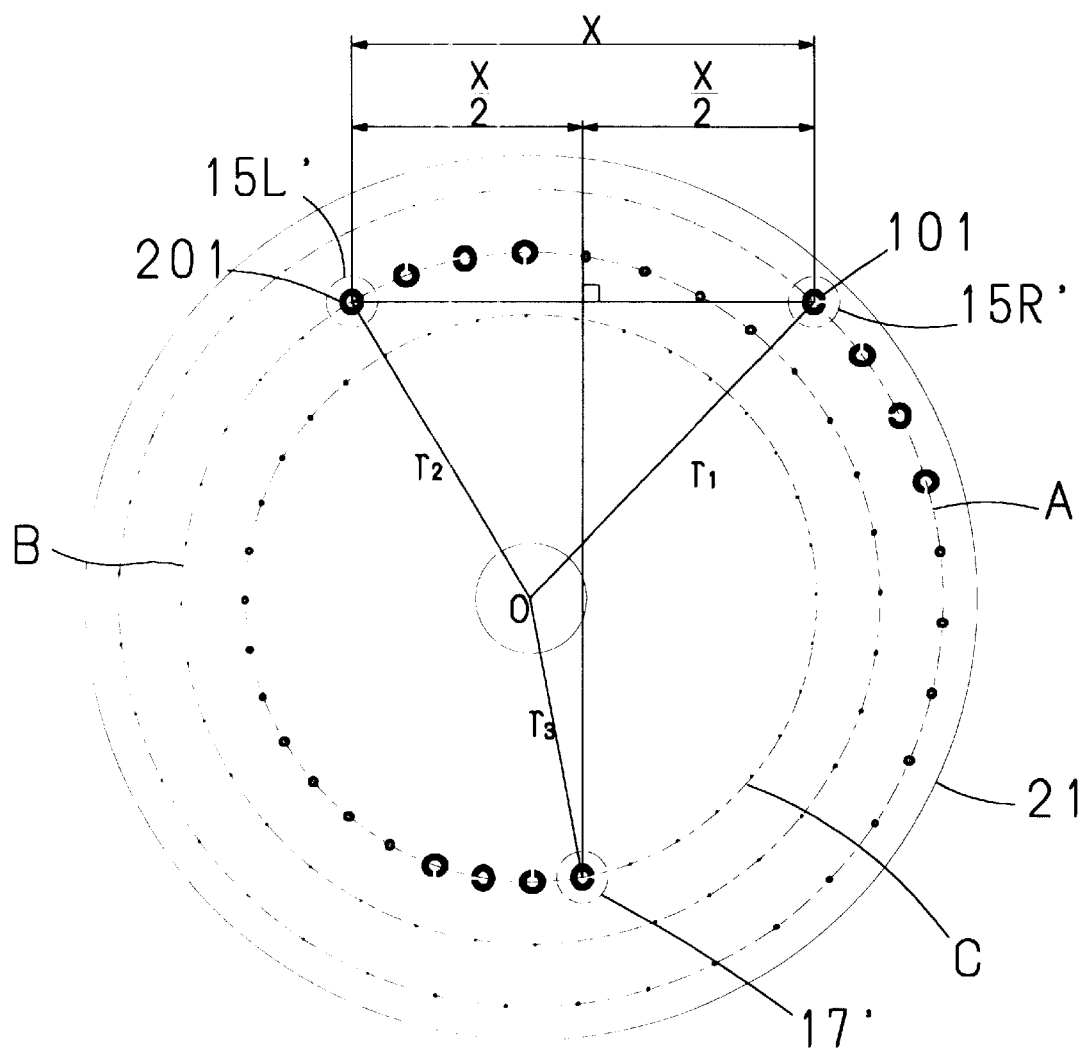
FIG. 4 is a view showing a rotating optometric chart disk in detail.

Next, explanation is given to the optometric chart formed on the disk 21 referring to FIG. 4. The plate of the disk 21 is made of a white plate glass and therefor transparent. On the disk 21, various optotypes for far vision measurement of right eye are aligned in order along a circumference of a first circle having a radius of r1 from a rotation center O of the disk 21, and these optotypes form a far vision optotype line A for right. Also on the disk 21 is a far vision optotype line B for left formed with far vision optotypes for left aligned in order along a circumference of a second circle having a radius of r2 from the rotation center O. The far vision optotype lines A and B respectively for right and left comprising the same set of optotypes lined in the same order so as to make pairs. To be more specific, there formed Landolt rings in 12 different patterns corresponding to visual acuity of 0.1–1.0, 1.2 and 1.5, and with gaps in one of four orientations: up, down, right and left. The Landolt rings are formed by chrome coating having shading characteristic.

Positional relationship among each optotype forming the far vision optotype lines A and B respectively for right and left is as follows. That is, when a far vision optotype 101 for right (the optotype corresponding to visual acuity of 0.1 having a gap oriented in the right) on the far vision optotype line A for right comes at the center of the far vision window 15R (indicated with a doted circle 15R' in FIG. 4), a far vision optotype 201 for left (the optotype corresponding to visual acuity of 0.1 having a gap oriented in the right) on the far vision optotype line B for left, which is a counterpart of the far vision optotype 101 for right, also comes to the center of the far vision window 15L (indicated with a doted circle 15L' in FIG. 4). The other optotypes alined on the on the far vision optotype lines A and B in order are also positioned such that the corresponding and identical optotypes have the same positional relationship relative to each other.

Here, the distance between the far vision windows 15R and 15L is designed to be equal to the interpupillary distance under convergent condition at the time when an examinee having a normal interpupillary distance looks at an object five meters away. That is to say, the distance between the far vision windows 15R and 15L is designed to be equal to the distance X between each pair of the corresponding optotypes, which are identical to each other, alined on the far vision optotype lines A and B.

As described above, the pairs of far vision optotypes for right and left formed on the disk 21 are arranged to have the same relative positional relationship to the far vision windows 15R and 15L respectively. Therefore, when the examinee observes inside of the main body 1 with both eyes, the far vision optotypes for right and left are easily fused into one image.

Further, a near vision optotype line C is formed with the near vision optotypes aligned along a circumference of a third circle having a radius of r3 from the rotation center O. Similarly to the far vision optotype lines A and B, there are Landolt rings in 12 different patterns corresponding to visual acuity of 0.1–1.0, 1.2 and 1.5 with gaps in one of four orientations: up, down, right and left. The near vision window 17 (indicated in a doted circle 17' in FIG. 4) for presenting a near vision optotype lined on the near vision optotype line C is determined its height so that the near vision window 17 is located on the perpendicular bisector of the line connecting the far vision windows 15R and 15L, and also on the near vision optotype line C.

The luminous flux of a near vision optotype presented in the near vision window 17 is bended its optical path by the mirror 28 and 27, as illustrated in FIG. 2, to be directed to the eyes ER and EL. Here, the angle θ that the near vision optical path L2 forms with the far vision optical path L1 and also the positions of the mirrors 28 and 27 are determined such that the near vision optotype is directed to the eyes ER and EL through a near portion of a standard progressive addition lens or bifocal lens that the examinee wears. As the result, even when a far vision optotype and a near vision optotype are presented at different heights, the both type of optotypes can be formed on one disk, the disk 21 in this case, while keeping the size small.

It is possible to form all the optotypes: pairs of far vision optotypes for right and left and near vision optotypes, on one line along a circumference of one circle. However, in the case of forming many kinds of optotypes, the disk inevitably becomes large, which is not desirable. On the other hand, if far vision optotypes for right and left and near vision optotypes are aligned on different circles as described above, the disk can be even smaller and thus the over all apparatus can be more compact.

Hereinafter, operations of the apparatus having the above configuration will now be described referring to FIG. 5 showing configuration of the operation panel 3 provided with switches thereon. This apparatus is provided with three examination modes: a manual mode, an auto mode (in which examination is carried out in accordance with the program by examinee's switch operations following the voice-guide) and a semi-auto mode (in which examination is carried out in accordance with the program by examiner's switch operations consistent with examinee's oral responses). Any of the modes may be selected with the use of a mode-selecting switch 40. Here, explanation is given mainly to the auto mode.

At a push of the start switch 6 by the examiner (or by the examinee), the control unit 30 turns on the LEDs 12R and 12L and the LEDs 24R and 24L, and also present optotypes corresponding to visual acuity of 0.1 in the far vision windows 15R and 15L. The voice-guide saying, "Please hold the lever lightly with your right hand and put your left hand by the buttons in the front, then look into the windows," is generated from the speaker 9. Thereafter, the voice-guide saying, "Your visual acuity will be measured, Please tilt the lever lightly in the direction of the gap in the ring, When you can not tell the direction, please press the button in the front," is generated. When the examinee responses with the joystick 5, the visual acuity examination program is initiated to run.

The visual acuity examination is programmed to perform far vision measurement and near vision measurement respectively in the order starting from right eye measurement, left eye measurement and then binocular measurement. First, an initial optotype which is the one corresponding to visual acuity of 0.5 is presented in the far vision window 15R for the right eye measurement. Here, the visual field of the left eye is under the same condition as the eye being occluded as long as the LED 12L for illuminating inside of the window and the LED 24L for illuminating optotypes are turned off.

Under the control by the control unit 30, the announce saying, "Which is the direction of a gap?" is made from the speaker 9 and instructs the examinee to tilt the joystick 5 in that directing if he can determine the direction. In response to the determination of the gap orientation in the optotype inputted with the joystick 5 by the examinee, the control unit 30 judges whether it is right or wrong. If the determination is correct, an optotype corresponding to visual acuity that is one level higher than the previous one is presented. If it is wrong on the other hand, an optotype corresponding to visual acuity that is one level lower than the previous one is presented. In the case where the examinee's determination is wrong, or in the case of receiving input from the response button 4 indicating the optotype is not legible to him when presenting the optotype that is one level higher than the previous one, visual acuity is then set once again for the previous acuity value, and then the examination goes on with an optotype of that acuity level but with a different gap orientation. In this manner, the optotype presented to the examinee is changed sequentially according to the program. upon judging the examinee's determinations, if more than two optotypes are correctly identified on one visual acuity level, the control unit 30 then credits the examinee with visual acuity of that level.

When far vision examination is completed on the right eye, left eye examination and then binocular examination are performed in the like manner, thereby obtaining examination results from each examination. At the completion of the binocular examination, the voice-guide from the speaker 9 says, "Far vision measurement has been completed, Next, visual acuity at a distance of 40 cm from your side is measured, To start the measurement, please tilt the lever, To cancel the measurement, please press the button in the front." In response to operations of the joystick 5 by the examinee, the near vision examination program is initiated to run.

The control unit 30 turns of f all the LEDs for far vision measurement, opens the shutters 18R and 18L covering the near vision windows 7R and 7L and turns on the LEDs 13 and 26. The control unit 30 controls to generate the voice-guide from the speaker 9 to say, "Please tilt the lever lightly in the direction of the gap in the ring, When you can not tell the direction, please press the button in the front." Thereafter, a near vision optotype corresponding to visual acuity of 0.5 is presented in the near vision window 17 and binocular near vision examination is performed according to the examination program in the like manner.

This near vision examination on downgaze produces accurate examination results because the examinee can gaze downward at the near vision optotype simply by tuning his eyeballs with the position he took for the far vision examination.

In the case of examination in the manual mode, the examiner selects either the far vision examination or the near vision examination with switches 42a and 42b to perform the thereby selected examination. In addition, the examiner selects the visual acuity to present an optotype of that level with the use of a switch 45a, and also selects an orientation of the gap in the optotype to be presented with the use of switches 46a–46d arranged in the middle of the panel 3. In response to these switch operations, an intended optotype is selected and presented to the examinee. The examiner asks the examinee about the determination of the optotype orientation and carries out the examination while making sure whether the examinee's oral response is right or wrong with illumination of the LEDs 37a–37d. The examinee's visual acuity is successively displayed in 45b and the value displayed at the completion of the examination is the measurement result.

In the manual mode, selection of the individual eye examination for right eye or left eye or the binocular examination is made with a switch 41. When the right eye is selected for the near vision examination, the shutter 18R is opened while the shutter 18L is opened when the left eye is selected. This allows the near vision examination to be performed on the right eye or on the left eye individually.

As has been described, if lines of optotypes both for right eye and for left eye are formed on one rotating optometric chart disk and therefore only one motor is required for driving the disk to rotate, positions of the optotypes presented for right eye and for left eye are prevented from being deviated in relation with each other. As the result, images of the two optotypes are easily fused into one. However, even in the case of using two disks and two motors to rotate the disks, it is still possible to fuse images of optotypes into one in the following way.

Figure 6A:
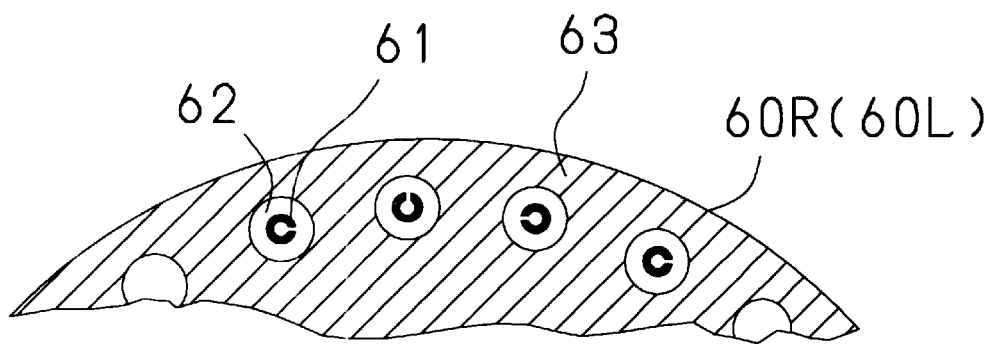
FIGS. 6A and 6B are views showing a modification example of the rotating optometric chart disk.
Figure 6B:
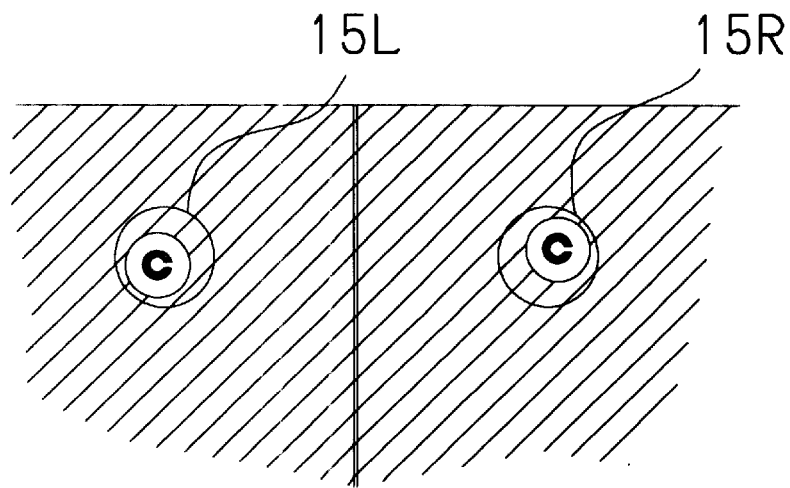

As shown in FIG. 6A, a rotating optometric chart disk 60R for right eye, and a rotating optometric chart disk 60L for left eye are provided with a light transmitting portions 62 (background portion which encircles an optotype 61) (since the rotating optometric chart disk 60L is the same as the disk 60R for right eye, it is not illustrated in the figure). In addition, an outer surrounding area 63 is painted with the same color as that of the covers 11R and 11L. In this way, as shown in FIG. 6B, when the optotypes 61 is positioned in the windows 15R and 15L (the openings should be appropriately large to some extent), the boundary between the window and the disk is not recognized. Therefore, by forming the light transmitting portion 62, two optotypes are fused into one image without any difficulty even though the positions of the optotypes for each eye relative to the respective windows 15R and 15L differ to some extent. It goes without saying that this scheme can be used in the case of forming optotypes for right and left on one disk.

The outer surrounding area 63 done not necessarily have to be painted with the same color as that of the covers 11R and 11L as long as the light transmitting portions 62 are distinguished (It is not necessary to shut the light totally).

As has been described above, according to the present invention, even in the case of presenting optotypes to right eye and reft eye separately through optical paths which are independently provided for respective eyes, images of the optotypes are fused into one easily on binocular vision. Accordingly, the examination can be carried out accurately.

According to the present invention, in addition, optotypes for right eye and for left eye are formed on one disk but along different circles. Therefore, even in the case of forming a number of optotypes on one disk, it is not necessary to upsize the disk and thus the apparatus can be compact in size.

Further, since the apparatus of the present invention requires a minimum set of optical elements, the apparatus can be configured at low cost.

Still further, according to the present invention, the near vision measurement on downgaze is performed with an examinee taking a natural position so that accurate examination results are obtained. In addition, the present invention realizes a simple configuration of the apparatus that performs both far vision measurement and near vision measurement. Thus the apparatus can be compact and inexpensive.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optometric chart presenting apparatus which has a casing provided with a pair of test windows for right eye and for left eye for presenting an optotype optically placed at a predetermined distance to an eye to be examined through at least one of the test windows within the casing, the apparatus comprising:

a rotating optometric chart disk having a set of optotypes for right eye and a set of optotypes for left eye on one surface thereof;

restricting means disposed on a side of the eye relative to the optotypes for restricting a visual field of the eye; and driving means for activating rotation of the rotating optometric chart disk in order to move an intended optotype into the visual field.

2. The optometric chart presenting apparatus according to claim 1, wherein the rotating optometric chart disk has a set of far vision optotypes for right eye and a set of far vision optotypes for left eye and each set of the optotypes are respectively aligned on circumferences of circles having different radius from a rotating center of the disk.

3. The optometric chart presenting apparatus according to claim 1, wherein the casing includes a casing for right eye provided with the test window for right eye and a casing for left eye provided with the test window for left eye, and the apparatus further comprising:

first illumination means for illuminating inside of the casing for right eye and of the casing for left eye respectively;

second illumination means for illuminating the optotypes for right eye and the optotypes for left eye respectively; and illumination control means for controlling the first illumination means and the second illumination means, and wherein the illumination control means controls the first illumination means and the second illumination means to achieve either releasing of both eyes, shielding of one of the eyes, or shielding of both eyes by turning on and off the first illumination means and the second illumination means.

4. The optometric chart presenting apparatus according to claim 1, wherein the rotating optometric chart disk has light transmitting portions as backgrounds of the optotypes and a light shading portion which is an outer area surrounding the light transmitting portions.

5. The optometric chart presenting apparatus according to claim 4, wherein a color of the light shading portion is generally the same as that of a visual field boundary area in the restricting means.

6. The optometric chart presenting apparatus according to claim 1, wherein the restricting means is part of an inner wall of the casing.

7. The optometric chart presenting apparatus according to claim 1, wherein the optotypes for right eye and the optotypes for left eye include identical counterparts to be presented in pairs simultaneously.

8. An optometric chart presenting apparatus which has a casing provided with a pair of far vision test windows for right eye and for left eye as well as a pair of near vision test windows below the far vision windows for presenting an optotype placed optically at a predetermined distance to an eye to be examined through at least one of the test windows within the casing, the apparatus comprising:

a rotating optometric chart disk having sets of far vision optotypes for right eye and for left eye as wall as a set of near vision optotypes on one surface thereof;

restricting means disposed on a side of the eye relative to the optotypes for restricting a visual field of the eye; and driving means for activating rotation of the rotating optometric chart disk in order to move an intended optotype into the visual field.

9. The optometric chart presenting apparatus according to claim 8, wherein each set of the optotypes are respectively aligned on circumferences of circles having different radius from a rotating center of the disk.

10. The optometric chart presenting apparatus according to claim 8, further comprising a mirror which reflects a luminous flux of a near vision optotype thereby adjusting a central axis thereof, and whereby an examinee wearing a multifocal lens can observe both a far vision optotype and a near vision optotype merely by turning the eye.

11. The optometric chart presenting apparatus according to claim 8, wherein the near vision test windows include:

a near vision test window for right eye;

a near vision test window for left eye; and shielding means which can shield each of the near vision test windows individually.

12. An optometric chart presenting apparatus which has a casing provided with a pear of test windows for right eye and for left eye for presenting an optotype placed optically at a predetermined distance to an eye to be examined through at least one of the test windows within the casing, the apparatus comprising:

a rotating optometric chart disk for right eye having a set of optotypes for right eye;

a rotating optometric chart disk for left eye having a set of optotypes for left eye;

restricting means disposed on a side of the eye relative to the optotypes for restricting a visual field of the eye; and driving means for activating rotation of each rotating optometric chart disk individually or in synchronism in order to move an intended optotype into the visual field, and wherein each disk has light transmitting portions as backgrounds of the optotypes and a light shading portion which is an outer area surrounding the light transmitting portions, and a color of the light shading portion is generally the same as that of a visual field boundary area in the restricting means.

13. The optometric chart presenting apparatus according to claim 12, wherein the restricting means is part of an inner wall of the casing.

14. The optometric chart presenting apparatus according to claim 12, wherein the optotypes for right eye and the optotypes for left eye include identical counterparts to be presented in pairs simultaneously.

15. The optometric chart presenting apparatus according to claim 12, wherein the casing includes a casing for right eye provided with the test window for right eye and a casing for left eye provided with the test window for left eye, and the apparatus further comprising:

first illumination means for illuminating inside of the casing for right eye and of the casing for left eye respectively;

second illumination means for illuminating the optotypes for right eye and the optotypes for left eye respectively; and illumination control means for controlling the first illumination means and the second illumination means, and wherein the illumination control means controls the first illumination means and the second illumination means to achieve either releasing of both eyes, shielding of one of the eyes, or shielding of both eyes by turning on and off the first illumination means and the second illumination means.

16. An optometric chart presenting apparatus for presenting an optotype for right eye and an optotype for left eye which are placed optically at a far distance to eyes to be examined by placing each optotype alternately into a pair of optotype presenting windows for right eye and for left eye provided in the casing, the apparatus comprising:

a rotating optometric chart disk having a set of optotypes for right eye and a set of optotypes for left eye on one surface thereon, each set of optotypes for right eye and for left eye are formed at such positions where positional relationship therebetween corresponds to that of the presenting windows for right eye and for left eye, whereby an optotype for right eye and an optotype for left eye to be presented in a pair simultaneously to the eyes are fused into one image on binocular observation; and rotating means for rotating the rotating optometric chart disk in order to present an intended optotype to the eye.

17. The optometric chart presenting apparatus according to claim 16, wherein each set of the optotypes are respectively aligned on circumferences of circles having different radius from a rotating center of the disk.

18. The optometric chart presenting apparatus according to claim 16, wherein the rotating optometric chart disk has light transmitting portions as backgrounds of the optotypes and a light shading portion which is an outer area surrounding the light transmitting portions, and a color of the light shading portion is generally the same as that of a visual field boundary area in the presenting windows.

19. An optometric chart presenting apparatus for presenting an optotype for right eye and an optotype for left eye which are placed optically at a far distance to eyes to be examined by placing each optotype alternately into a pair of optotype presenting windows for right eye and for left eye provided in the casing, the apparatus comprising:

a rotating optometric chart disk for right eye having a set of optotypes for right eye;

a rotating optometric chart disk for left eye having a set of optotypes for left eye; and rotating means for rotating the rotating optometric chart disks individually or in synchronism in order to present an intended optotype to the eye, and wherein each set of optotypes for right eye and for left eye are formed at each disk in such positions where positional relationship therebetween corresponds to that of the presenting windows for right eye and for left eye, whereby an optotype for right eye and an optotype for left eye to be presented in a pair simultaneously to the eyes are fused into one image on binocular observation, each disk has light transmitting portions as backgrounds of the optotypes and a light shading portion which is an outer area surrounding the light transmitting portions, and a color of the light shading portion is generally the same as that of a visual field boundary area in the presenting windows.

* * * * *

UNITED STATES PATENT AND TRADEMARK OFFICE
CERTIFICATE OF CORRECTION

PATENT NO. : 6,244,713 B1
DATED : June 12, 2001
INVENTOR(S) : Akihiro Hayashi

It is certified that error appears in the above-identified patent and that said Letters Patent is hereby corrected as shown below:

Column 11, claim 12,
Line 18, "pear" should read -- pair --.

Signed and Sealed this

Fifteenth Day of January, 2002

Attest:

Attesting Officer

JAMES E. ROGAN
Director of the United States Patent and Trademark Office